United States Patent [19]

Allan et al.

[11] 3,953,304
[45] Apr. 27, 1976

[54] ELECTROPLATING BATHS FOR NICKEL AND BRIGHTENER-LEVELER COMPOSITIONS THEREFOR

[75] Inventors: John L. Allan, Glen Rock; Kollengode V. Srinivasan, Saddle Brook; Philip D. Readio, Sparta, all of N.J.; Judit Cestero, New York, N.Y.

[73] Assignee: Dart Industries Inc., Los Angeles, Calif.

[22] Filed: June 23, 1975

[21] Appl. No.: 589,114

[52] U.S. Cl............................. 204/49; 204/DIG. 2; 260/294.8 R; 260/295 R; 260/295 A; 260/295 AM
[51] Int. Cl.²................. C25D 3/16; C07D 213/55
[58] Field of Search............... 204/49, 43 T, DIG. 2; 106/1; 260/294.8 R, 295 R, 295 A, 295 AM

[56] References Cited
UNITED STATES PATENTS

| 2,658,867 | 11/1953 | Little | 204/49 |
| 3,190,821 | 6/1965 | Todt | 204/49 |

FOREIGN PATENTS OR APPLICATIONS

| 2,160,737 | 7/1973 | France | 204/49 |
| 932,843 | 7/1963 | United Kingdom | 204/49 |

*Primary Examiner*—G. L. Kaplan
*Attorney, Agent, or Firm*—Fred S. Valles; Bryant W. Brennan; Margareta LeMaire

[57] ABSTRACT

An aqueous acid nickel electroplating bath containing as a brightener-leveling agent the reaction product of an acetylenic diester of a halogenated saturated aliphatic acid with a heterocyclic compound containing a tertiary nitrogen atom. The brightener may have the general formula

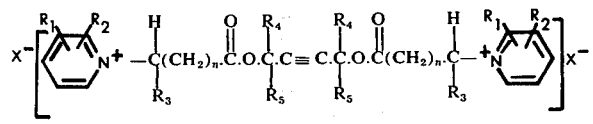

wherein $R_1$ and $R_2$ are hydrogen, halogen or a hydroxy, carboxy, carboxyester, sulphoxy, alkyl, amino or amido group;
$R_3$ is a hydrogen or an alkyl group;
$R_4$ and $R_5$ are hydrogen or an alkyl group;
X is halogen and
n is an integer from 0 to 2.

19 Claims, No Drawings

ELECTROPLATING BATHS FOR NICKEL AND BRIGHTENER-LEVELER COMPOSITIONS THEREFOR

BACKGROUND OF THE INVENTION

The present invention relates to novel brightener-leveler compositions useful in nickel electroplating and to a process for electroplating bright and level nickel surfaces onto metal substrates. It is already well known to use brightening agents in the acid plating baths to promote the formation of a bright nickel surface on articles to be plated. A variety of such brighteners are in commercial use and commonly include mixtures of acetylenic alcohols, and organic sulpho-oxygenated compounds, such as aliphatic or aromatic sulfonates or corresponding acids.

One serious disadvantage is that the leveling action of the known brightening agents is poor, resulting in only moderately bright nickel deposits. Another disadvantage is the brittleness of the nickel deposits obtained with these brighteners.

In order to overcome the aforementioned disadvantages it is common to include additional components in the plating bath e.g. saccharin for the purpose of promoting the deposition of more ductile nickel coating. Although saccharin, which is a sulfo-oxygenated compound, is sometimes referred to as a brightener, it does not by itself yield bright nickel plating but acts primarily as a stress reducer. A leveling agent is also included to promote the formation of a smoother surface of the plated out nickel. One such leveling agent of particular interest is the one disclosed in French Patent No. 2,160,737. The agent is a quaternary compound obtained by reacting an acetylenic mono-ester of a halogenated saturated aliphatic acid with a heterocyclic compound having a tertiary nitrogen. The resulting acetylenic quaternary compound is required to be used in combination with an organic sulpho-oxygenated compound. When these compounds are added to a plating bath, enhanced brilliance and leveling of the nickel deposits were said to be obtained. In further studies, however, which were carried out for the purpose of evaluating the aforementioned compounds of the French patent as leveling agents, it was found that although leveling was improved to a certain degree, their performance could only be rated as average.

It is therefore a general object of the present invention to provide a novel-brightener-leveling agent having improved properties over those of the prior art compositions.

THE INVENTION

It has been found in accordance with the present invention that quaternary compounds of the general structure given below when included in acid nickel plating baths result in bright, ductile coatings of excellent leveling.

The novel compounds can be expressed by the general formula:

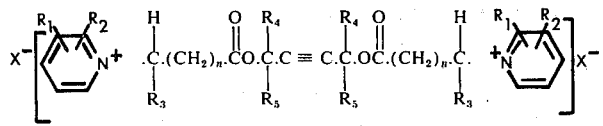

wherein $R_1$ and $R_2$ each can be hydrogen, halogen or a hydroxy, carboxy, carboxy ester, sulphoxy, alkyl, amino or amido group, $R_3$ is hydrogen or an alkyl group
$R_4$ is hydrogen or an alkyl group
$R_5$ is hydrogen or an alkyl group
X is a halogen, and
$n$ is an integer from 0 to 2.

The novel compounds may be obtained in a two step process wherein first a monohalogenated aliphatic acid is reacted with an acetylenic diol in a molar ratio of about 2:1 to produce the acetylenic diester of the halogenated saturated aliphatic acid having the general chemical structure defined by

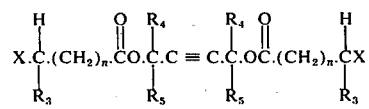

wherein $R_3$, $R_4$, $R_5$, X and n are defined as before. The acetylenic diester is subsequently reacted with a heterocyclic compound containing a tertiary nitrogen atom in a molar ratio of about 1:2.

Suitable monohalogenated saturated aliphatic acids include, monohaloacetic acids, halo-2-propionic acids, halo-3-propionic acids, halo-2-butyric acids, halo-3-butyric acids and halo-4-butyric acids. Chlorine or bromine is the preferred halogen. Due to its ready availability and relatively low cost the most preferred monohalogenated saturated aliphatic acid is monochloroacetic acid.

Acetylenic diols that can be used include 2-butyne-1,4-diol; 3-hexyne-2,5-diol and 2,5-dimethyl-3 hexyne-2-5-diol. 2-butyne-1,4-diol is the preferred acetylenic diol.

The heterocyclic compound containing a tertiary nitrogen is selected from heterocyclic tertiary bases having the general formula:

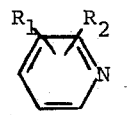

or salts thereof with organic or inorganic acids wherein $R_1$ and $R_2$ are defined as before. Suitable heterocyclic compounds of this nature include pyridine, quinoline, isoquinoline, picoline, methylethyl pyridine, 3-chloro pyridine, 3-hydroxy pyridine, 8-hydroxy quinoline, pyridine-3-sulphonic acid, nicotinic acid, isonicotinic acid, 6-hydroxy nicotinic acid, methyl nicotinate, ethyl nicotinate, phenyl nicotinate and the like.

The first step of the reaction is suitably carried out at elevated temperatures such as 70°–110°C in the presence of an esterification catalyst such as sulfuric acid, p-toluene sulfonic acid or the like. Provisions should be made for removal of water formed in the reaction in order to promote the formation of the acetylenic diester of the halogenated acid. The reaction may be carried out in the absence of any solvent or in the presence of a solvent such as benzene. The reaction product, which is insoluble in water, may be subjected to one or more washes including an alkaline wash for neutralization purposes. If desired, a pure crystalline product may be obtained by removal of solvent, if present, and subsequent recrystallization from a suitable solvent such as an alcohol, e.g. methyl alcohol, or a liquid hydrocarbon e.g. heptane.

In the second step the acetylenic bis-ester reaction product of the first step is reacted with the heterocyclic nitrogen compound in the presence of a suitable solvent such as benzene, or in the presence of water, at elevated temperatures e.g. 40°–110°C. The quaternization reaction usually takes place in a few hours to several days depending upon the particular system and temperatures used. In case a solvent such as benzene is used in the second stage reaction system, there is no need to remove any solvent originating from the first stage. The final product is obtained as a precipitate, which is collected by filtration, washed with solvent and dried in vacuum to remove any residual solvent.

In case water is used in the second stage reaction system, any solvent present from the first stage reaction should be removed from the bisester prior to charging it to the reactor. The final product is obtained directly as an aqueous solution. The progress of the second stage conversion can be monitored directly by analysis of titrable halogen.

The compounds of this invention can be used in concentrations of from about 0.01 to about 1.0 g/liter of plating solution. When used as a dual function brightener-leveling agent the concentration may range from about 0.1 to about 1.0 g/liter and when used primarily as a leveling agent in combination with other brighteners the concentration may range from about 0.01 to about 0.5 g/liter.

As a brightener-leveling agent it is preferred that it be used in combination with a stress-reducer such as saccharin compound, which for the purpose of this invention is intended to include such compounds as alkali metal saccharinates, e.g. sodium saccharinate, or nuclearly substituted saccharins, e.g. O-sulfobenzoic imide having a nuclear substituent, e.g. an alkyl, halo- or sulpho-substituent. The concentration of the saccharin compound should be maintained within the range of from about 0.2 to about 5 g/liter of plating solution and preferably in the range of about 0.5 to about 2.5 g/l. No other brightener is essential in the plating batch, however, it is within the scope of this invention to add auxiliary brighteners such as acetylenic alcohols, e.g. 2-butyne-1,4-diol, 1-butyne-3-ol, propargyl alcohol and the like as well as various organic sulfoxy compounds, e.g. aliphatic or aromatic sulfonates and the like, to further enhance the throwing power of the brightener. Other additives which may be used include anti-pitting agents, wetting agents etc., as is well known in the art.

The brightener-leveling agent of the present invention is useful in any type of nickel electroplating bath. The source of nickel is a nickel salt such as nickel sulfate, usually in combination with boric acid and nickel chloride, nickel fluoborate or an alkaline chloride such as sodium or ammonium chloride in concentration well known in the art. The plating conditions using such baths are also well known in the art and include temperatures in the range of 30°–70°C, a pH of the plating bath of from about 2.5 to 5.5 and a cathode current density in the range of 2 to 100 amps/sq. ft.. The cathode (article to be plated) may be mechanically agitated or the plating solution may be agitated by pumping or air circulation therethrough or a combination of the aforementioned methods of agitation may be employed.

For a better understanding of the invention the following examples are presented.

EXAMPLE 1

A quaternary compound in accordance with this invention was prepared using the techniques set forth below.

A solution of 86 grams (1.0 mole) by 2 butyne-1,4-diol, 189 grams (2.0 mole) monochloroacetic acid and 2 grams p-toluene sulfonic acid in 500 ml benzene was refluxed for 14 hours in a laboratory apparatus equipped with a Dean-Stark trap. At the end of this period 32 ml water had been collected. The warm solution was washed twice with 250 ml water and twice with 10% sodium bicarbonate and then filtered through calcium chloride. Benzene was removed by evaporation to yield a residue, which upon cooling gave 175 grams of a brown solid having a melting point of 58°–61°C. Recrystallization of this material in 650 ml methyl alcohol gave 144 grams of bis-1,4(chloroacetoxy)-2-butyne as light yellow crystals having a melting point of 61°–62°C. Further recrystallization of the bis-ester from heptane resulted in white crystals having a melting point of 62°–62.5°C. Analyses of the latter product for carbon and hydrogen content showed excellent agreement between theoretical and observed values. The observed carbon concentrations on duplicate samples were 40.00 and 40.23 wt.% (theoretical 40.17%) and the hydrogen concentrations of duplicate samples were found to be 3.35 and 3.38 wt. % (theoretical 3.35%).

For the second reaction step a solution was prepared of 16 grams (0.063 mole) of the bis-ester recrystallized from methylalcohol, and 9.92 grams (0.126 mole) pyridine in 50 ml. benzene in a closed reaction vessel, and the solution was maintained at 50°C for 3 days. The precipitate which was formed was collected by filtration, washed with benzene and dried in a vacuum oven to give 18 grams (72.3%) of the final bis-pyridinium chloride product.

EXAMPLE 2

The same compound was prepared in this example using another technique for the second reaction step. Thus a mixture of 6.2 grams (0.026 mole) of the methyl alcohol recrystallized bisester of Example 1, 4.6 grams (0.058 mole) pyridine and 100 ml water was refluxed for about 4 hours, after which time solution had occurred. Titration of an aliquot of the reaction mixture with silver nitrate indicated the presence of 0.050 mole $Cl^-$. Formation of the bis-pyridinium chloride was therefore 96% complete.

EXAMPLES 3–5

The reaction product of pyridine and 1,4-bis(-chloroacetoxy)-2-butyne was evaluated for its effectiveness as a nickel brightener in Example 3 in a 1-liter cell using a nickel anode and a brass cathode which was premachined to a uniform surface roughness. The average current density was 20 amps/sq. ft.. A combination of cathode rod movement and air agitation of the solution was employed. The duration of the test was 20 minutes. The plating bath was maintained at a pH of 4.0 and a temperature of 60°C. and had the following composition:

TABLE 1

| Ingredient | Plating bath Concentration gm/l |
|---|---|
| Nickel Sulfate | 300 |
| Nickel Chloride | 60 |
| Boric Acid | 50 |

To this bath was added 0.5 gm/liter each of the aforementioned bispyridinium chloride and sodium saccharinate. The nickel plating produced in the test had good brightness, good leveling, good ductility and average throwing.

(1) described in U.S. Pat. No. 3,007,861

For comparison purposes two similar tests were carried out (Examples 4 and 5 using a compound prepared according to French Patent No. 2,160,737 involving reaction in a first step of equal molar quantities of monochloroacetic acid, and 2-butyne-1,-4-diol and then the quaternization reaction of the reaction product of step 1 with a stoichiometric quantity of pyridine. The resulting compound had the chemical formula:

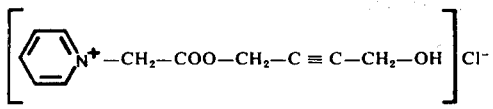

0.4 gm/l of this compound and 0.5 gm/l sodium saccharinate was added in Example 4, to the electrolyte of Table 1 and the test was carried out as in Example 3. The resultant nickel plating had similar properties to the one produced in Example 3, except that the leveling was no more than average when compared on a scale ranging from poor to excellent.

In Example 5, the concentration of the prior art compound was increased to 0.7 gm/l, all other conditions being the same as in Example 3. No improvement in leveling was observed with the aforementioned increase in concentration, and a more brittle plating was obtained.

EXAMPLES 6–8

The procedure of Example 3 was followed in these examples, except that various amounts of organic sulfonates were also added to the electrolyte to improve the throwing power.

In Example 6, four runs were made where sodium napthalene-1,3,6-tri-sulfonate was added in concentration of 0.5, 1.0, 1.5 and 2 grams per liter respectively. The throwing power increased with increased concentrations of the sulfonate and at 2 grams per liter the rating was very good.

Four runs were made in Example 7 using sodium vinyl sulfonate in respective concentrations of 0.15, 0.3, 0.6 and 1.2 grams per liter. The throwing power increased as the concentration was increased to 0.6 grams per liter, where very good throwing was observed. Doubling the concentration to 1.2 grams per liter did not result in any further improvement.

Sodium allyl sulfonate was used in Example 8 in concentrations of 0.2, 0.4, 0.8 and 1.6 gms/liter. The throwing power increased with increasing concentration up to 0.8 grams per liter. Good throwing was observed at this level as well as at 1.6 grams per liter.

EXAMPLES 9–11

These comparative experiments were carried out to demonstrate the excellent performance of the compound of the invention primarily as a leveling agent. The tests were carried out with the nickel electrolyte and test procedures of Example 3.

In Example 9, 20 ml/l of a commercial nickel brightener obtained under the tradename ELECTRO-BRITE 720M from Electrochemicals, Youngstown, O., was added to the nickel electrolyte. The nickel plating was bright, ductile, with good throwing but poor leveling as evident from the fact that the original surface roughness of the brass panel was still seen over the nickel plating.

In Example 10, 0.2 grams per liter of the inner salt of pyridine-1,4 bis(chloroacetoxy)-2-butyne was also added to the electrolyte. The nickel plating on the brass panel was brighter, ductile and was marked by a high degree of smoothness. Most of the surface roughness was leveled out.

By increasing the concentration of the aforementioned inner salt to 0.4 grams per liter in Example 11 more leveling and smoothness was obtained.

It will be apparent to those skilled in the art that various modifications and substitutions may be made to the specific embodiments herein set forth by way of examples without departing from the scope of the invention.

What is claimed is:

1. A plating bath for the electroplating of nickel comprising an aqueous acidic solution of at least one nickel salt and from about 0.01 to about 1.0 grams per liter of a quaternary compound having the general formula

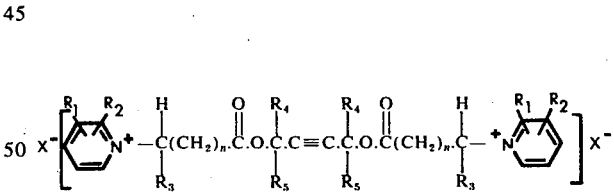

wherein $R_1$ and $R_2$ are hydrogen, halogen or a hydroxy, carboxy, carboxyester, sulphoxy, alkyl, amino or amido group;

$R_3$ is hydrogen or an alkyl group;

$R_4$ and $R_5$ are hydrogen or an alkyl group;

X is a halogen and n is an integer from 0 to 2.

2. The plating bath of claim 1 wherein X is a chlorine or a bromine.

3. The plating bath of claim 1, wherein $R_1$ and $R_2$ each is a hydrogen.

4. The plating bath of claim 1, wherein $R_3$ is a hydrogen and $n$ is 0.

5. The plating bath of claim 1 wherein $R_4$ and $R_5$ each is a hydrogen.

6. The plating bath of claim 1, wherein the quaternary compound is the reaction product of pyridine and 1,4 bis(chloroacetoxy)-2-butyne and having the formula

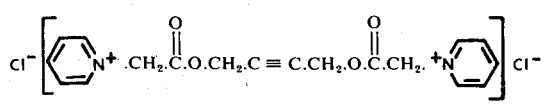

7. The plating bath of claim 1, wherein the quaternary compound is added in concentrations from about 0.01 to about 0.5 grams per liter primarily as a leveling agent in cooperations with at least one other brightener.

8. The plating bath of claim 1 wherein saccharin is present in concentrations from about 0.2 to about 5.0 grams per liter.

9. The plating bath of claim 8 wherein the quaternary compound is present in concentrations of from about 0.1 to about 1.0 grams per liter.

10. The plating bath of claim 9 also containing at least one other organic sulfoxy compound.

11. The plating bath of claim 10 wherein the organic sulfoxy compound is sodium naphthalene-1,3,6-trisulfonate.

12. The plating bath of claim 10, wherein the organic sulfoxy compound is sodium vinyl sulfonate.

13. The plating bath of claim 10, wherein the organic sulfoxy compound is sodium allyl sulfonate.

14. A quaternary compound having the general formula

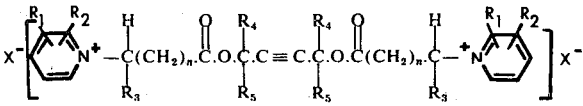

wherein $R_1$ and $R_2$ are hydrogen, halogen or a hydroxy, carboxy, carboxyester, sulphoxy, alkyl, amino or amido group;

$R_3$ is hydrogen or an alkyl group;

$R_4$ and $R_5$ are hydrogen or an alkyl group;

X is a halogen and $n$ is an integer from 0 to 2.

15. The quaternary compound of claim 14 wherein X is a chlorine or a bromine.

16. The quaternary compound of claim 14 wherein $R_1$ and $R_2$ each is a hydrogen.

17. The quaternary compound of claim 14 wherein $R_3$ is a hydrogen and $n$ is 0.

18. The quaternary compound of claim 14 wherein $R_4$ and $R_5$ each is a hydrogen.

19. The quaternary compound of claim 14 wherein the quaternary compound is the reaction product of pyridine and 1,4 bis(chloroacetoxy)-2-butyne and having the formula

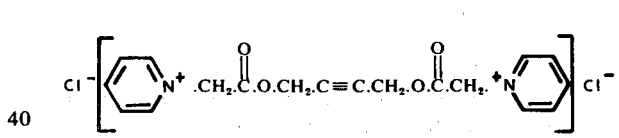

* * * * *

UNITED STATES PATENT AND TRADEMARK OFFICE
CERTIFICATE OF CORRECTION

PATENT NO. : 3,953,304
DATED : April 27, 1976
INVENTOR(S) : John L. Allan, Kollengode V. Srinivasan, Philip D. Readio, and Judit Cestero It is certified that error appears in the above-identified patent and that said Letters Patent are hereby corrected as shown below:

Column 3, line 53, "batch" should read --bath--

Column 4, line 68, after "cell" insert --$^{(1)}$--

Column 6, claim 3, line 1, "$R_1$ and R" should read --$R_1$ and $R_2$--

Signed and Sealed this

Twenty-seventh Day of July 1976

[SEAL]

Attest:

RUTH C. MASON
Attesting Officer

C. MARSHALL DANN
Commissioner of Patents and Trademarks